United States Patent
Kania

(10) Patent No.: US 6,443,913 B1
(45) Date of Patent: *Sep. 3, 2002

(54) APPARATUS AND METHOD FOR RELIEVING MOTION SICKNESS

(76) Inventor: Bruce Kania, P.O. Box 5186, Bozeman, MT (US) 59717

( * ) Notice: Subject to any disclaimer, the term of this patent is extended or adjusted under 35 U.S.C. 154(b) by 0 days.

This patent is subject to a terminal disclaimer.

(21) Appl. No.: 09/520,226

(22) Filed: Mar. 7, 2000

(51) Int. Cl.[7] .......................... A61B 5/117; A61B 19/00; A62B 17/00; F16K 17/36
(52) U.S. Cl. .................. 600/595; 128/898; 128/202.11; 137/38
(58) Field of Search .......................... 600/27, 595, 484, 600/546; 381/98, 1; 137/38; 340/945; 128/898, 202.11

(56) References Cited

U.S. PATENT DOCUMENTS

| | | |
|---|---|---|
| 1,907,402 A | 5/1933 | Fedor |
| 2,288,683 A | 7/1942 | Clancy |
| 2,745,091 A | 5/1956 | Leffler |
| 3,461,423 A | 8/1969 | Trumble |
| 3,548,400 A | 12/1970 | Boyd |
| 3,610,227 A | 10/1971 | Griffin |
| 4,016,535 A | 4/1977 | Dinlocker |
| 4,052,720 A | 10/1977 | McGregor et al. |
| 4,070,463 A | 1/1978 | Graybiel |
| 4,267,547 A | 5/1981 | Sugiyama |
| 4,283,798 A | 8/1981 | Kuehn |
| 4,284,987 A | 8/1981 | Gibson et al |
| 4,408,196 A | 10/1983 | Freeman |
| 4,508,510 A | 4/1985 | Clifford |
| 4,528,559 A | 7/1985 | Freeman |
| 4,562,589 A | 12/1985 | Warbaka et al. |
| 4,647,928 A | 3/1987 | Casey et al. |
| 4,697,174 A | 9/1987 | Viator, Sr. |

(List continued on next page.)

OTHER PUBLICATIONS

U.S. application No. 09/263,777, filed Mar. 5, 1999, pending.
U.S. application No. 09/458,814, filed Dec. 10, 1999, pending.

(List continued on next page.)

Primary Examiner—Eric F. Winakur
Assistant Examiner—Nikita R Veniaminov

(57) ABSTRACT

A method and apparatus used for relieving motion sickness, in which a sensor senses a property of an object and a sensory converter coupled to the sensor converts the sensed motion to related sensory signals for presentation to a user. The sensory signals include, for example, audio signals, display signals, electronic stimulation, mechanical stimulation, white noise, etc. The audio, electrical and mechanical sensory signals have a variation in spectral emphasis related to the sensed motion, such as by varying a bandwidth, a center frequency, and an amplitude of a first range of the sensory signals. The display signals have a variation in a display characteristic and the audio tone signals have a variation in time intervals between successive audio tones. The audio tones may also include audio messages containing words. The sensory signals are used to resolve a conflict between vestibular, ocular, and proprioceptive inputs of the user, thus relieving motion sickness. The apparatus also includes ON/OFF switches configured to turn ON and OFF desired components within the apparatus. Further, the properties sensed by the sensor may be exaggerated.

39 Claims, 9 Drawing Sheets

U.S. PATENT DOCUMENTS

| | | | |
|---|---|---|---|
| 4,777,170 A | | 10/1988 | Heinrich |
| 4,817,149 A | | 3/1989 | Myers |
| 4,817,633 A | | 4/1989 | McStsravick et al. |
| 4,925,878 A | | 5/1990 | Bodó et al. |
| 4,929,228 A | | 5/1990 | Hendricks |
| 4,930,435 A | | 6/1990 | Newman |
| 4,992,443 A | | 2/1991 | Chelen |
| 5,033,694 A | | 7/1991 | Sato |
| 5,067,941 A | | 11/1991 | Hendricks |
| 5,119,754 A | | 6/1992 | Martinez et al. |
| 5,120,739 A | | 6/1992 | Chelen |
| 5,121,744 A | * | 6/1992 | Njemanze ............... 128/202.11 |
| 5,143,081 A | | 9/1992 | Young et al. |
| 5,161,196 A | | 11/1992 | Ferguson |
| 5,209,712 A | | 5/1993 | Ferri |
| 5,303,715 A | | 4/1994 | Nashner et al. |
| 5,353,242 A | | 10/1994 | Crosbie et al. |
| 5,367,297 A | | 11/1994 | Yokoyama |
| 5,425,378 A | | 6/1995 | Swezey et al. |
| 5,603,334 A | | 2/1997 | Sharp |
| 5,613,690 A | | 3/1997 | McShane et al. |
| 5,629,848 A | | 5/1997 | Repperger et al. |
| 5,645,077 A | | 7/1997 | Foxlin |
| 5,647,835 A | * | 7/1997 | Martineau ................... 600/27 |
| 5,694,939 A | | 12/1997 | Cowings |
| 5,791,982 A | | 8/1998 | Curry et al. |
| 5,807,284 A | | 9/1998 | Foxlin |
| 5,829,446 A | | 11/1998 | Tiffany |
| 5,857,980 A | * | 1/1999 | Wilson ....................... 600/546 |
| 5,966,680 A | | 10/1999 | Butnaru |
| 6,042,533 A | | 3/2000 | Kania |
| 6,228,021 B1 | * | 5/2001 | Kania .......................... 600/27 |
| 2001/0000459 A1 | * | 4/2001 | Kania .......................... 381/98 |

OTHER PUBLICATIONS

U.S. application No. 09/520,226, filed Mar. 7, 2000, pending.

Discovery, vol. 14, No. 19, Oct. 5, 1990, Brooks AFB, Texas, "Study Opens Ears on 3–D Sound" By Capt Alvin Mitchell, ASK Office of Public Affairs Wright–Patterson, AFB, Ohio.

AOPA Pilot, Dec. 1989, pp 65–69, "The Art of Noise", "Technology brings tranquility to the cockpit", By Marc E. Cook.

Technology, Time, Dec. 4, 1989, p. 94, "Fighting Noise with Antinoise", Electronic mufflers cancel unwanted sound waved in midair, By Philip Elmer–Dewitt.

Aviation, Space, and Environmental Medicine, Aug. 1989, pp. 779–785, "Performance and Well–being Under Tilting Conditions: The Effects of Visual Reference and Artificial Horizon" By A. Rolnick, Ph.D., and W. Bless, Ph.D.

Aviation, Space, and Environmental Medicine, Aug. 1990, pp. 699–706, "The Effects of Acoustics Orientation Cues on Instrumental Flight Performance in a Flight Simulator" By Terence J. Lyons, M.D., M.P.H., Ken K. Gillingham, M.D., Ph.D., Don C. Teas, Ph.D., William R. Ercoline, M.S., and Carolyn Oakley, B.A.

Comparative Studies of Hearing in Vertebrates, Popper, AN., Fay, R.R.(eds). New York, Springer–Verlag, 1980, pp. 357–373, Chapter 12, "Directional Hearing in Terrestrial Mammals", By George Gourevitch of the Department of Psychology, Hunter College of the City University of New York.

* cited by examiner

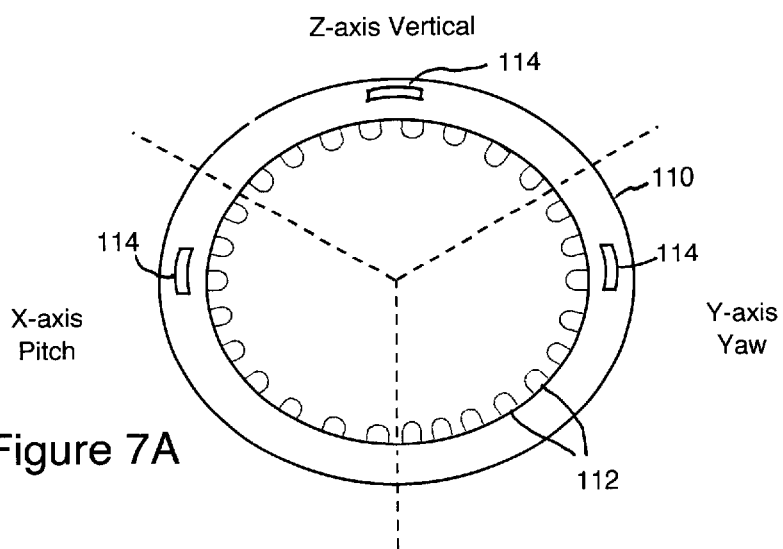
Figure 7A
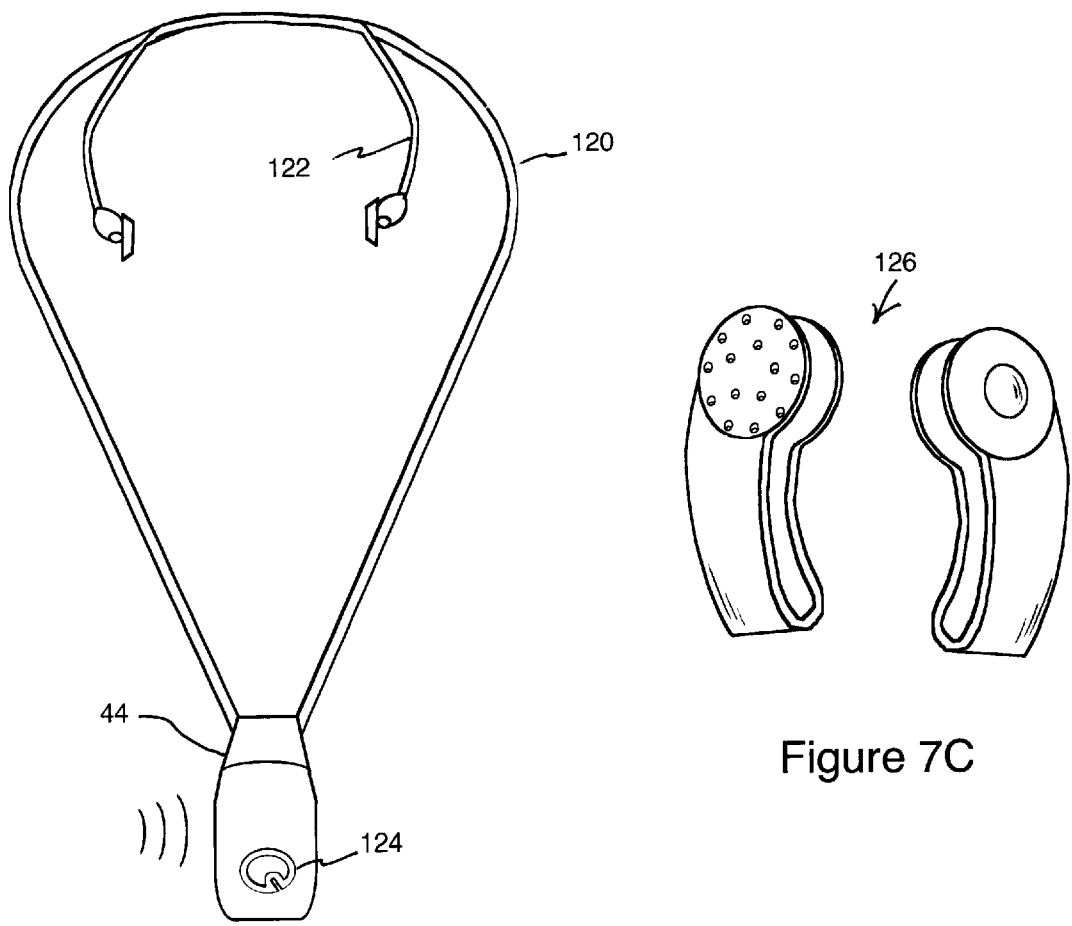
Figure 7B
Figure 7C

APPARATUS AND METHOD FOR RELIEVING MOTION SICKNESS

CROSS-REFERENCE TO RELATED APPLICATIONS

This application is related to co-pending applications Ser. No. 09/121,720, filed on Jul. 24, 1998, and Ser. No. 09/263,777, filed on Mar. 5, 1999, both of which are incorporated in their entirety.

BACKGROUND OF THE INVENTION

1. Field of the Invention

The present invention relates to a method and apparatus for preventing or relieving motion sickness. More particularly, the present invention relates to providing sensory signals corresponding to a property (e.g., position or motion) of an object so the individual may use these signals to improve a sense of equilibrium. The present invention also relates to a Motion Obfuscation Device (MOD) for obscuring motion sickness conflicting signals to improve a sense of equilibrium of the individual.

2. Discussion of the Background

Essentially, motion sickness occurs as a result of an unusual motion experience. Until a person can adapt to these unusual motions, motion sickness can occur. The phenomenon of motion sickness may be derived from a principle researched by Dr. David Winters, a retired University of Waterloo professor, and which is referred to as "The Principle of Indeterminacy."

The principle of indeterminacy describes a human's natural ability to identify changes in the neuromuscular skeletal system and to adapt to a new optimum motion. For example, if a prosthetic leg does not offer comparable function, an amputee will favor the remaining leg. Thus, the residual limb becomes weaker and the remaining leg becomes stronger. The option to utilize the prosthesis or the natural leg represents a conflict, i.e., between walking in a conventional symmetrical manner or favoring the natural leg. The person, without conscious volition, chooses favoring the natural side when the choice is perceived by the human's body as optimal. Currently, it is not known for certain which senses are most influential in making this choice. However, it is likely that pain and comfort, proprioceptive, vestibular, and ocular inputs affect this choice.

Similarly, motion sickness results from a conflict between these vestibular, ocular and proprioceptive inputs. For example, conventional wisdom among charter boat operators is charter boat captains do not get seasick, unless they spend a significant amount of time below deck, whereas captains of cruise ships are known to be somewhat more susceptible to motion sickness. This is because a charter boat captain usually sits high in the cabin, a position from where he can observe quite clearly what the relatively small charter boat is about to experience. Thus, he has accurate visual data which reconciles a conflict between the vestibular, ocular, and proprioceptive inputs. On the contrary, the captain of a large cruise ship cannot see what is taking place immediately in front of the ship's bow. Thus, a conflict between the vestibular, ocular, and proprioceptive data is not resolved.

Motion sickness is very costly for many industries. For example, the airline industry loses millions of dollars per year from passengers who are unwilling to travel because they experience motion sickness. The same can be said for cruise ships. In addition, if a person experiences motion sickness while operating a dangerous vehicle, injury or even a loss of life may occur.

Thus, a need for a device which relieves or prevents motion sickness will have a significant impact on society. The co-pending applications Ser. No. 09/121,720 and Ser. No. 09/263,777, describe an apparatus for relieving motion sickness which includes a sensor which senses a motion of an object and a sensory converter coupled to the sensor for converting the sensed motion to corresponding sensory signals having a variation in spectral emphasis in proportion to the sensed motion. Also included is a presentation mechanism for presenting the sensory signals to the user. Thus, a user may use the converted sensory signals to resolve a conflict between vestibular, ocular, and preoceptive inputs. After further research and experimentation, the inventor of this application, which is the same as the inventor in the co-pending applications, has discovered additional novel features which will be described in the present application.

SUMMARY OF THE INVENTION

An object of the present invention is to provide a novel apparatus and method for relieving motion sickness.

Another object of the present invention is to relieve motion sickness by presenting a user with an audio signal (e.g., white noise) that obfuscates conflicting signals from the inner ear.

Yet another object of the present invention is to relieve motion sickness by presenting a user with exaggerated signals corresponding to sensed properties of an object.

Another object of the present invention is to relieve motion sickness which may occur during video games including virtual reality games.

Still another object of the present invention is to relieve motion sickness by presenting a user with at least one signal including, for example, audio, visual, electrical, magnetic, mechanical, or combinations thereof which have a variation related to a sensed property of an object, so that the user may resolve a conflict between vestibular, ocular, and proprioceptive inputs. The object whose property is sensed may be a vessel the user is in or on, for example, or it may the user. The object may be referenced to the vessel, or be referenced to an arbitrary reference point. For an audible signal, the information may be presented in the form of a modulated noise or pseudo-noise, where the modulation includes, for example, a variation in a bandwidth, a center frequency, and an amplitude of a first range of the sensory signals. Visual display signals may be presented on a display as display elements having, for example, a shape, a size, an intensity, and a color. For example, the display elements may include a blue square, red circle, green star, etc. In addition, the display elements may have a variation in a display characteristic, such as a variation in a size, a shape, an intensity, and a color of the display elements. The variation in display characteristic is related to the sensed property of the object. In addition, the sensory signals may include audio tone signals which have a variation in time intervals between successive tone signals. The variation in time intervals is related to the sensed motion of the object.

These and other objects of the present invention are achieved by providing an apparatus which includes a sensor which senses an attitude or motion of an object, or some derivative thereof, and a sensory converter which converts the sensed motion to corresponding sensory or control signals. In addition, the sensory signals are presented to a user by using, for example, a transmitter and receiver. Thus, the user receives the sensory signals and is able to resolve a conflict between vestibular, ocular, and proprioceptive inputs via the principle of indeterminancy. The sensory signals may be, for example, any one of audio, video, white noise, pink noise, brown noise, popcorn noise, optical signals, audio tones, or any combination thereof, etc.

BRIEF DESCRIPTIONS OF THE DRAWINGS

A more complete appreciation of the invention and many of the attendant advantages thereof will be readily obtained as the same becomes better understood by reference to the following detailed description when considered in connection with the accompanying drawings, wherein:

FIG. 7A is a perspective view of a wristband for presenting sensory signals to a user according to the present invention;

FIG. 7B is a perspective view of a pendant receiver/transmitter for presenting sensory signals to a user according to the present invention;

FIG. 7C is a perspective view of speaker earrings for presenting sensory signals to a user according to the present invention;

DESCRIPTION OF THE PREFERRED EMBODIMENTS

Figure 1:
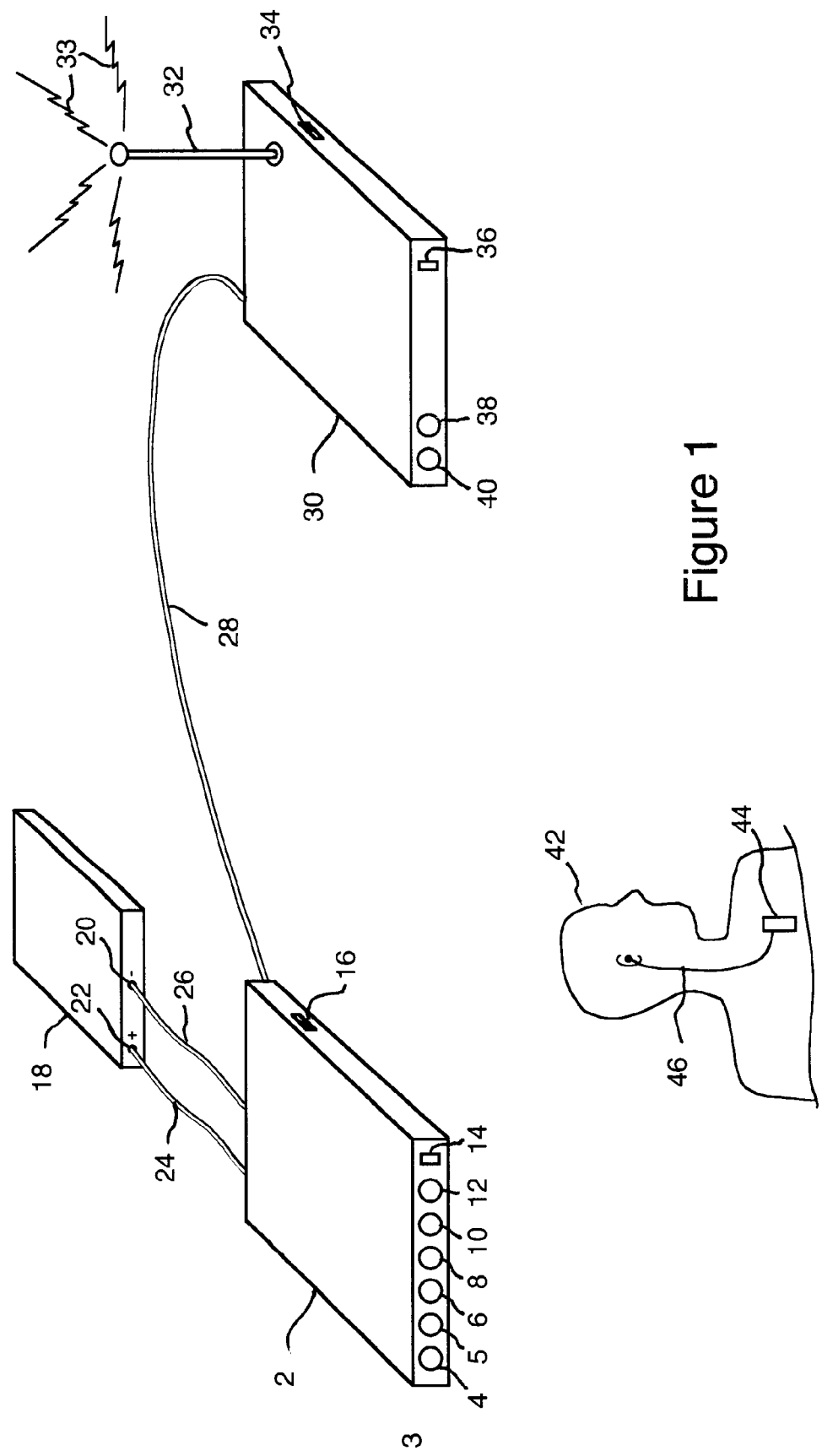
FIG. 1 is a perspective view of an apparatus for relieving motion sickness according to the present invention.
Figure 2A:
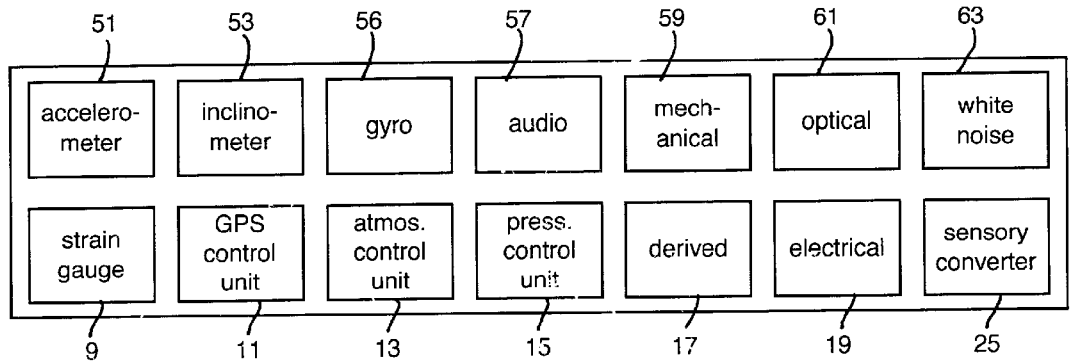
FIG. 2A is a block diagram illustrating components of an inertia processor device according to the present invention.

Referring now to the drawings, wherein like reference numerals designate identical or corresponding parts throughout the several views, FIG. 1 illustrates an apparatus for relieving motion sickness including an inertia processor 2 connected to a battery 18 and a transmitter 30. Also shown is a receiver 44 attached to an individual 42 for receiving a sensory signal 33 transmitted by the transmitter 30. The inertia processor 2 includes a front panel 3 which houses, for example, an audio volume control mechanism 4, a video control mechanism 5, a white, pink, brown or popcorn noise volume control mechanism 6, a pitch (x-axis) sensitivity control mechanism 8, a yaw (y-axis) sensitivity control mechanism 10, and a vertical (z-axis) sensitivity control mechanism 12. Other control mechanisms may also be included based on the components contained within the inertia processor 2. For example, FIG. 2A illustrates examples of several components which may be included in the inertia processor 2. Thus, the front panel 3 may include a mechanical control mechanism (not shown) for setting a desired amount of mechanical stimulation to the individual 42. The control mechanisms for the different types of stimulations (e.g., mechanical, optical, audio, etc.) may also be included with the receiver 44 (rather than with the inertia processor 2), for example. The inertia processor 2 also includes an appropriate bandpass filter (now shown) to achieve a desired bandwidth of the sensory signals.

The audio volume mechanism 4 and the white, pink, brown or popcorn noise volume mechanism 6 may be used to adjust the volume of the sensory signal 33 transmitted by the transmitter 30. The pitch sensitivity mechanism 8, the yaw sensitivity mechanism 10, and the vertical sensitivity mechanism 12 may be used to adjust the corresponding sensitivity of the inertia processor 2. That is, using the above-noted sensitivity mechanisms, a user may set the inertia processor 2 to be more or less sensitive in sensing a property of an object. Other sensing mechanisms may also be used, which will be discussed with reference to FIG. 2A.

The front panel also includes an LED power indicator 14, which indicates whether the power is on or off. For example, if the power is ON, the LED indicator 14 will be a green color. On a side portion of the inertia processor 2, a power switch 16 is used to turn ON and OFF the inertia processor 2. The inertia processor 2 also includes an appropriate number of RCA autojacks on a rear side of the instrument (not shown), which provide high impedance, low level output for audio, video, white noise, pink noise, brown noise, popcorn noise and audio tone signals, etc.

White noise is a random noise containing all frequencies and sounds similar to the "hiss" noise generated by an FM radio receiver when tuned off station. That is, white noise is a random noise that has a flat frequency spectrum at the frequency range of interest. In addition, pink, brown or popcorn noise signals may also be used. Pink noise is a random noise whose spectrum level has a negative slope of 10 decibels per decade (i.e., any noise with a power spectrum that falls as a power spectrum of 1/f), and brown noise has a power spectrum of $1/f^2$. The name "brown noise" comes from Brownian motion, which is the random motion of small objects in fluids. Ordinary music tends to have a brown power spectrum, whereas white noise tends to sound noisy or busy, and pink noise sounds overly simple. Popcorn noise includes individual events whose magnitude distribution does not have a maximum at zero and is not even symmetric about zero. Popcorn noise includes isolated spikes in the output voltage and the voltage height of spikes has a mean value that is significantly (i.e., by more than a mV) different from zero. The audio tone signals include tone signals separated by time intervals (spaces).

The battery 18 includes a negative battery terminal 20 and a positive battery terminal 22, which connect to the inertia processor 2 via battery wires 24 and 26. In addition, the inertia processor 2 is connected to the transmitter 30 using a communication cable 28. Alternatively, the inertia processor 2 may be optically connected (e.g., using infrared signals) to the transmitter 30. That is, the inertia processor 2 may use wireless communication to communicate with the transmitter 30. The transmitter 30 includes an antenna 32, a power switch 34, and a power LED indicator 36. Also included is, for example, a multichannel control mechanism 38 and a volume control mechanism 40.

The control mechanisms (e.g., volume control mechanism 4 and yaw sensitivity control mechanism 10) are not limited to the locations shown in FIG. 1. For example, the control mechanisms may be placed on a side or top portion of the inertia processor 2, or be included with the receiver 44. Further, the battery 18, inertia processor 2, transmitter 30, and receiver 44 may be included in a single common housing.

The inertia processor 2 may be mounted or placed on a level (normally level) surface of an object. The inertia processor 2 senses a property of the object and converts this property to corresponding sensory signals for presentation to a user. The properties sensed may be, for example, motion, position, angular positions, etc. The audio, white noise, pink noise, brown noise, and popcorn noise sensory signals have a variation in spectral emphasis in proportion to the sensed property. The variation in spectral emphasis includes, but is not limited to, a variation in a bandwidth, a center frequency, and an amplitude of a first range of the sensory signals. For example, if the inertia processor 2 is configured to operate using audio signals, i.e., by connecting the audio output jack of the inertia processor 2 to the transmitter 30, the variation in spectral emphasis includes varying a frequency of, for example, a first signal within a first predetermined range around a first center frequency in proportion to a sensed pitching motion, for example, of the object.

Alternatively, if the inertia processor 2 is configured to operate using white, pink, brown or popcorn noise signals, the variation in spectral emphasis includes varying, for example, a first frequency range of the white, pink, brown or popcorn noise signals in proportion to a sensed pitching property of the object. In addition, if the inertia processor 2 is configured to operate using display signals, the display signals may be displayed as display elements which have a variation in a display characteristic corresponding to the sensed property of the object. The display elements may include, for example, red, green, and blue colors used in a conventional video display. The red, green and blue colors are altered in proportion to the sensed property of the object. Finally, if the inertia processor 2 is configured to operate using audio tone signals, the audio tone signals may have a variation in time intervals between successive audio tones based on the sensed motion of the object.

The sensory signals are presented to the user 42 using, for example, the transmitter 30 and receiver 44. The receiver 44 may be, for example, a pocket-sized receiver (see FIG. 13, for example), in order to receive the sensed sensory signals 33. The receiver 44 also includes, for example, an earphone 46 so the user may listen to the corresponding sensory signals. The user 42 may then use the sensory signals 33 transmitted by the transmitter 30, without conscious volition, to resolve a conflict between the vestibular, ocular, and propreoceptive inputs, thereby relieving motion sickness.

In addition, it should be noted that FIG. 1 illustrates the sensory signals being presented to the user 42 with a transmitter 30 and receiver 44. However, it is also possible to present the sensory signals to the user 42 via an earphone, for example, connected to the inertia processor 2. That is, the use of a separate transmitter 30 and receiver 44 is not required. The receiver 44 may also communicate with the user 42 via wireless headphones/earphones (discussed later).

FIG. 2A is a block diagram illustrating various components which may be contained within the inertia processor 2. As shown, the inertia processor 2 may include an accelerometer 51, an inclinometer 53, a gyro 56, an audio processor 57, a mechanical processor 59, an optical processor 61, and a white, pink, brown or popcorn noise processor 63 (hereinafter referred to as a white noise processor 63). Also shown is a strain gauge 9, a GPS control unit 11, an atmospheric control unit 13, a pressure control unit 15, a derived processor 17, an electrical processor 19, and a sensory converter 25. The sensing mechanisms shown in FIG. 2A include the accelerometer 51, inclinometer 53, gyro 56, strain gauge 9, GPS control unit 11, atmospheric control unit 13, pressure control unit 15 and derived control unit 17. The presentation mechanisms include the audio processor 57, mechanical processor 59, optical processor 61, white noise processor 63, and electrical processor 19. The inertia processor may include any variation of the components shown in FIG. 2A. For example, the inertia processor 2 may include three accelerometers, or one accelerometer and two inclinometers, etc.

The sensory converter 25 converts properties sensed by the sensing mechanisms and presents them to the user using the presentation mechanisms. For example, the accelerometer 51 senses a vertical motion of an object and the inclinometer 53 senses a yaw and/or pitching of the object. The sensory converter 25 converts this sensed motion to corresponding sensory signals for presentation to the user. In addition, the inertia processor 2 may include additional accelerometers and inclinometers, etc., so that the inertia processor 2 may sense a property in at least one of six degrees of freedom.

The audio processor 57 communicates the sensory signals as audio signals or audio tones to the transmitter 30. For example, the user may be wearing a pendant receiver/ transmitter which communicates the sensory signals received from the transmitter 30 to the user via wireless earphones (see FIG. 7B, for example). The mechanical processor 59 communicates the sensory signals as mechanical stimulations to the user. For example, the user may be wearing a wrist band which vibrates or applies pressure to the wrist (see FIG. 7A, for example) based on the sensory signals. In addition, the mechanical stimulation may be adjusted by the user to be faint, noticeable, or very strong, for example. The adjustments of the mechanical stimulation may be made via a dial on the wrist band or based on a control mechanism provided on the inertia processor 2. The optical processor 61 and white noise processor 63 respectively communicate the sensory signals as video signals and white, pink, brown or popcorn noise signals, to the transmitter 30. The electrical processor 19 is similar to the mechanical processor 15, but provides electrical impulses to the user. For example, a user may wear a wrist band which electrically stimulates the user using faint, noticeable or very strong electrical stimulations, for example. In addition, the optical processor 61 communicates the sensory signals as display signals.

As discussed above, the sensory converter 25 converts the property sensed by the sensors to corresponding sensory signals which are presented to the user by the presentation mechanisms. In addition, FIG. 2A illustrates the sensing and presentations mechanisms included in a common housing. However, these mechanisms may be separate from each other. For example, the presentation mechanisms may be included in a device (e.g., receiver 44) worn by the user 42 so the user may adjust the volume of the audio tones, etc.

Figure 2B:
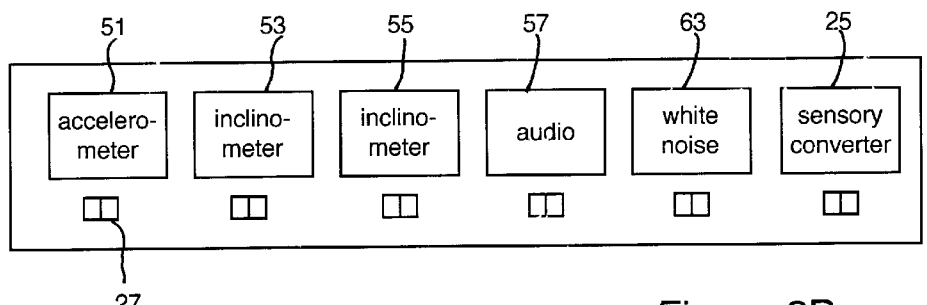
FIG. 2B is a block diagram illustrating the components of an inertia processor device mounted on a ship or ferry according to the present invention.

FIGS. 2B–2H illustrate different examples of inertia processors according to the present invention. For example, FIG. 2B illustrates an inertia processor 2 used aboard a ship or ferry. As shown, the inertia processor 2 may include the accelerometer 51, first inclinometer 53 and a second inclinometer 55, audio processor 57, white noise processor 63 and sensory converter 25. Also shown is a switch 27, which may be used to turn ON or OFF a respective mechanism. In this way, the user has the option of using either the audio processor 57 or white noise processor 63 or both. The user may also turn off the sensory converter 27 and merely listen to the audio processor 57 or white noise processor 63. In the example of FIG. 2B, the accelerometer 51, first inclinometer 53 and second inclinometer 55 sense a motion of the ship and the sensory converter 27 converts the sensed motion to corresponding sensory signals for presentation to the user by the audio processor 57 or white noise processor 63. The example in FIG. 2B may also include the optical processor 61, electrical processor 19, etc.

Figure 2C:
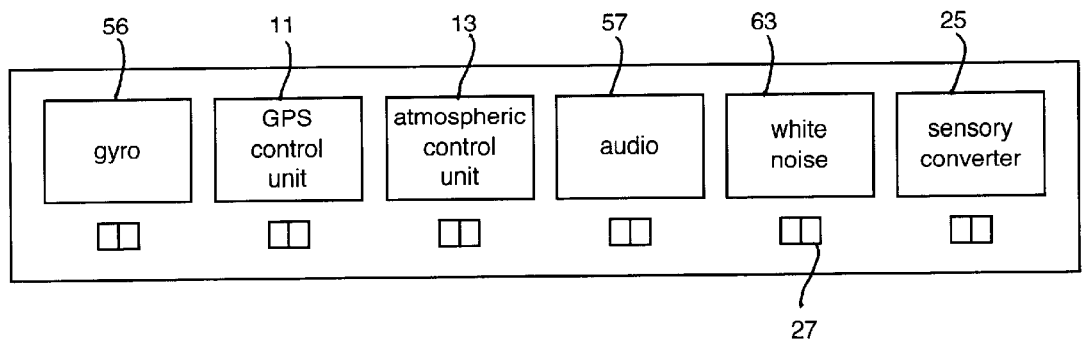
FIG. 2C is a block diagram illustrating the components of an inertia processor device mounted in an airplane or helicopter according to the present invention.

FIG. 2C illustrates an example of the inertia processor 2 used aboard an airplane or helicopter. The inertia processor 2 may include the gyro 56, GPS control unit 11, atmospheric control unit 13, audio processor 57, white noise processor 63 and sensory converter 25. In this example, the gyro 56 may be used to sense a motion of the aircraft and the sensory converter 25 converts this motion to corresponding sensory signals. Similarly, the GPS control unit 11 and atmospheric control unit 13 may also be used to respectively sense different positions and atmospheric pressures of the aircraft, and the sensory converter 25 converts these sensed properties to corresponding sensory signals to be presented to the user with the audio processor 57 or white noise processor 63. Because most aircraft already include GPS and atmospheric pressure systems, the inertia processor 2 may be configured to also receive this information (i.e., would not have to independently sense the positions and atmospheric pressures of the aircraft).

Figure 2D:
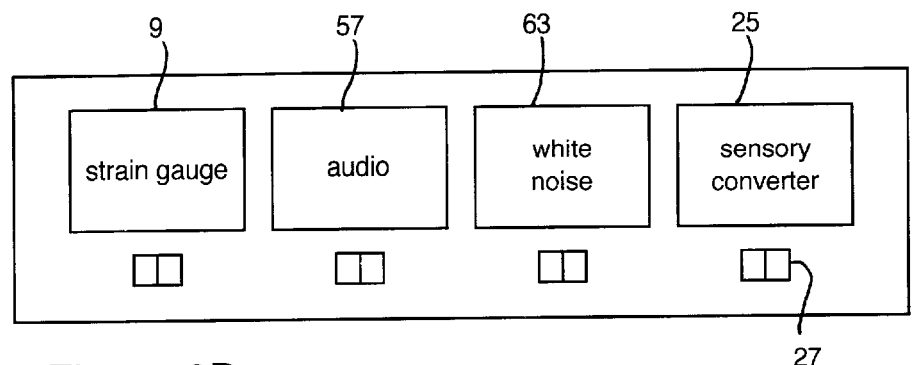
FIG. 2D is a block diagram illustrating the components of an inertia processor device mounted in an elevator according to the present invention.

FIG. 2D is an example of an inertia processor 2 used in an elevator. In this example, the strain gauge 9 may sense a strain on the elevator cable and this sensed property may be converted by the sensory converter 25 and presented to the user via the audio processor 57 or white noise processor 63. This example may be particularly beneficial to elevators in high-rise buildings, which may descend or ascend 60 or more floors. Many people become nauseous during the ascent or descent of the elevator, and by using the inertia processor 2, may prevent this motion sickness.

Figure 2E:
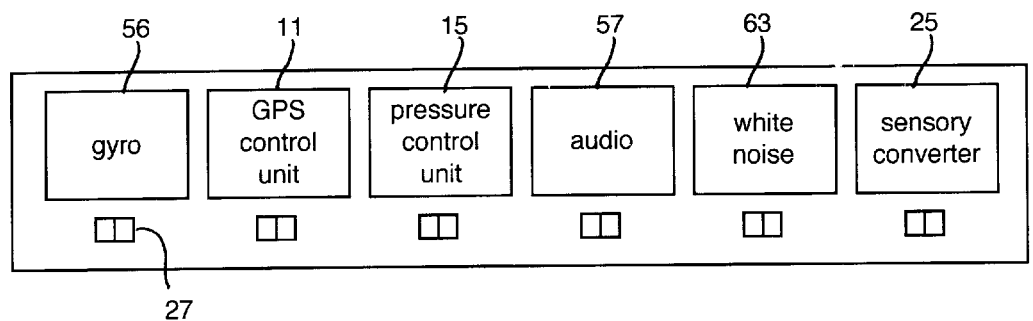
FIG. 2E is a block diagram illustrating the components of an inertia processor device mounted in a submarine according to the present invention.

FIG. 2E illustrates an example of the inertia processor 2 used aboard a submarine. In this example, the gyro 56 and GPS control unit 11 are the same as discussed above. The pressure control unit 15 senses the pressure the submarine is experiencing as it descends or ascends (again, many submarines already sense this property). The sensory converter 25 converts the sensed properties and the audio processor 57 or white noise processor 63 transmits the converted sensory signals to the user.

Figure 2F:
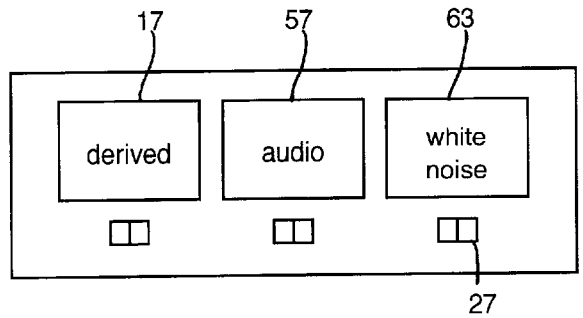
FIG. 2F is a block diagram illustrating the components of an inertia processor device which produces simulated control signals according to the present invention.

FIG. 2F illustrates an example of an inertia processor in which sensory signals are derived by the derived processor 17. That is, the derived processor 17 functions as a simulator which simulates a motion of an aircraft, ship, etc. The simulated signals may then be transmitted to the user via the audio processor 57 and white noise processor 63. For example, in some situations, the property sensed by a sensor is repetitive. That is, a ship at rest may experience repetitive motions of swaying side to side. In this instance, the motions may be derived or predicted and transmitted to the user (i.e., a sensory converter is not necessary).

Figure 2G:
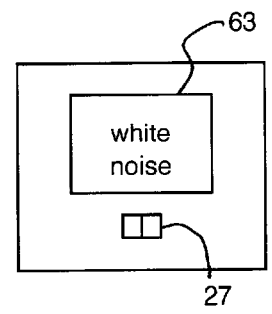
FIG. 2G is a block diagram illustrating the components of an inertia processor device which generates white noise according to the present invention.

FIG. 2G illustrates the Motion Obfuscation Device (MOD) according to the present invention for obscuring motion sickness conflicting signals to improve a sense of equilibrium of the individual. As shown, the inertia processor does not include a sensory converter 25 or a sensing mechanism (i.e, accelerometer 51, inclinometer 53, etc.). In more detail, during experiments performed by the inventor of the present invention, a first group of passengers aboard a ship were equipped with the inertia processor 2 shown in FIG. 2B. Another group of individuals were only provided with the white noise presentation mechanism 63. During very heavy seas (i.e., during a storm), it was determined in which a substantial amount of motion of the ship is occurring, some individuals may prefer to simply have white noise presented to them. That is, the white noise obfuscates the conflicting occular and vestibular signals.

In addition, each inertia processor 2 discussed above includes an ON/OFF switch 27 for one or all of the components contained within the inertia processor 2. Therefore, each inertia processor 2 may be configured to operate as the MOD. That is, a user may turn OFF all components except the white noise processor. Further, a user may customize the inertia processor 2 to one particularly suited to their needs. That is, a user may find that one inclinometer is more desirable than two inclinometers. In this instance, the user may turn OFF the second inclinometer 55.

The inertia processors 2 shown in FIG. 2A–2F illustrates the sensing mechanisms contained within a single housing. However, the sensing mechanisms may be disposed at positions on the ship, submarine, etc., so as to exaggerate a motion of the ship, submarine, etc. For example, the inclinometers 53 and 55 may be disposed at positions on a boat (or any other object) so as to exaggerate the motion of the boat. That is, the first inclinometer 53 may be placed at a position extending outward from the stern of boat and the second inclinometer 55 may be placed at a position extending outward from a bow of the boat. Thus, the inclinometers 53 and 55 detect an exaggerated motion of the boat. The exaggerated motions are converted by the sensory converter 25 and presented to the user via the audio processor 57 or white noise processor 63, for example. Alternatively, the inclinometers 53 and 55 contained in the single housing, may output signals which are exaggerated by, for example, a computer processor and then these exaggerated signals may be converted and transmitted to the user.

Figure 3:
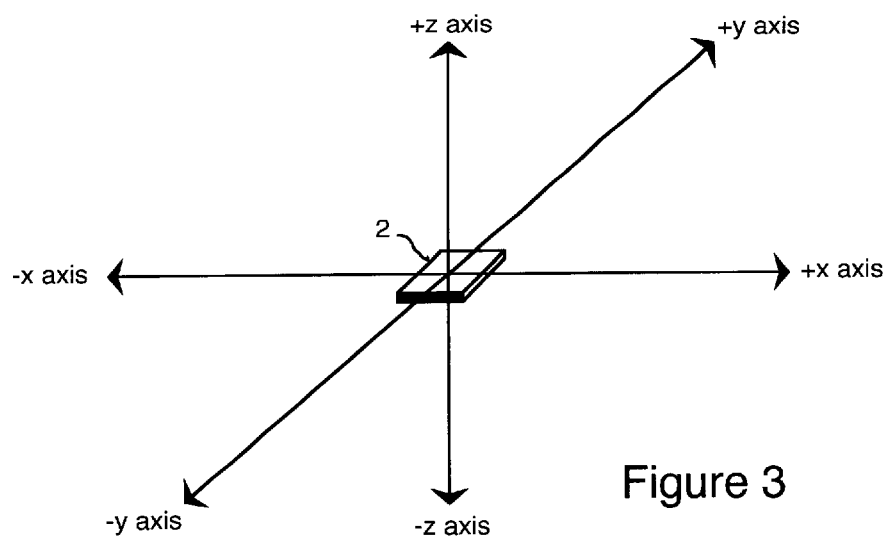
FIG. 3 illustrates a three-dimensional axis with respect to the inertia processor according to the present invention.

FIG. 3 illustrates a three-dimensional axis with respect to the inertia processor 2 shown in FIGS. 2A–2F (note FIG. 2G, illustrates the MOD which does not include a sensory converter). For example, the accelerometer 51 senses a vertical motion of the object along the vertical axis, designated as the z-axis. The inclinometers 53 and 55 detect inclination changes (i.e., pitching and yawing motions) about the horizontal plane designated as the x-axis and y-axis, respectively.

Figure 4A:
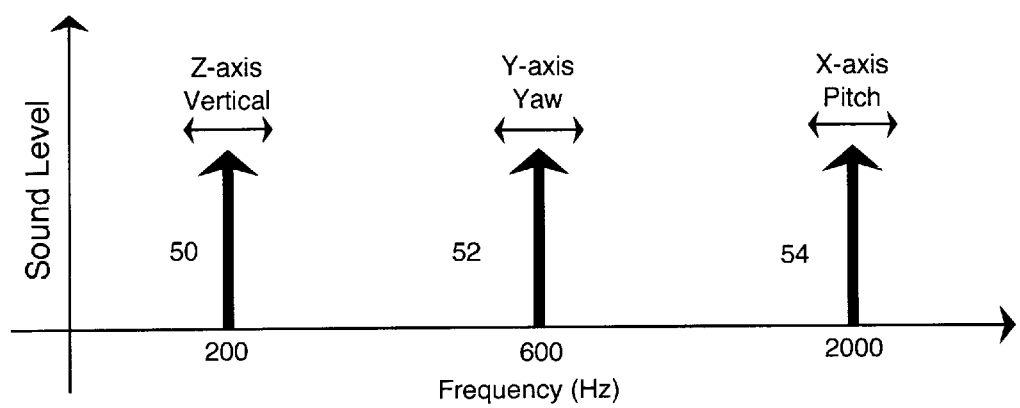
FIG. 4A is a graph illustrating frequencies of audio signals corresponding to vertical, yaw, and pitch motions sensed by the inertia processor according to the present invention.

FIG. 4A illustrates audio signals in response to motion sensed by the inertia processor 2 shown in FIG. 2B, for example. As shown, the inertia processor 2 generates three different audio signals which individually change in frequency in response to a sensed motion. The z-axis frequency tone 50, which may be centered at 250 Hz, for example, increases in frequency when a positive z-axis motion is sensed and decreases in frequency in response to a negative z-axis sensed motion. The z-axis vertical tone 50 shown in FIG. 4A is at 200 Hz, which represents a decrease of 50 Hz from the center frequency. That is, a negative z-axis motion was sensed by the accelerometer 51. The y-axis frequency tone 52, centered at 500 Hz, for example, increases in frequency when the instrument is tilted clockwise (when viewed from the front of the device) about the y-axis. This is referred to as a yaw to the right. In addition, the y-axis frequency tone 52 decreases in frequency when the instrument is tilted counter-clockwise about the y-axis, referred to as a yaw to the left. The y-axis frequency tone 52 shown in FIG. 4A is at 600 Hz, which represents an increase of 100 Hz from the center frequency. That is, a yaw to the right was sensed by the inclinometer 53. The x-axis frequency tone 54, centered at 2 KHz, for example, increases in frequency when the instrument is tilted forward, referred to as a forward pitch, and decreases in frequency when the instrument is tilted backwards, referred to as a rearward pitch. Thus, as shown, the x-axis frequency tone 54 has not changed, which indicates the second inclinometer 55 did not detect a pitching motion. In addition, the changes to the tone frequencies are proportional to the sensed motion, that is, the greater the sensed motion, the greater the tone change. However, the proportional relationship is not necessarily linear and may be empirically determined. The representation of the center tone frequencies of 250 Hz, 500 Hz, and 2 KHz are for illustration purposes only and other values may be used.

Figure 4B:
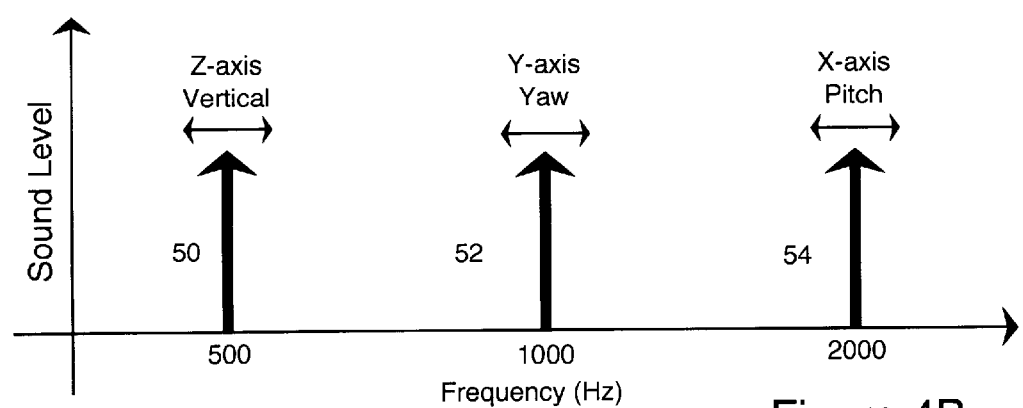
FIG. 4B is another graph illustrating frequencies of audio signals corresponding to vertical, yaw, and pitch motions sensed by an inertia processor according to the present invention.

For example, FIG. 4B illustrates the z-axis frequency tone 50, the y-axis frequency tone 52, and the x-axis frequency tone 54 centered at frequencies of 500, 1000, and 2000 Hz, respectively. The frequency tones increase and decrease in response to a sensed motion, as described in reference to FIG. 4A. Through experimentation, it has been determined that the human ear is particularly sensitive to frequencies around 1000 Hz. Further, it has been determined that the y-axis yaw motion is particularly critical in causing motion sickness. Therefore, in FIG. 4B, the y-axis frequency tone 52 (i.e., y-axis yaw motion) is centered at 1000 Hz.

Further, FIGS. 4A and 4B correspond to motion sensed in three degrees of freedom. As discussed above, the inertia processor 2 may detect motion in at least six degrees of freedom. Thus, if six degrees of freedom were sensed, it is possible to represent this by six tones rather than three tones.

Figure 5A:
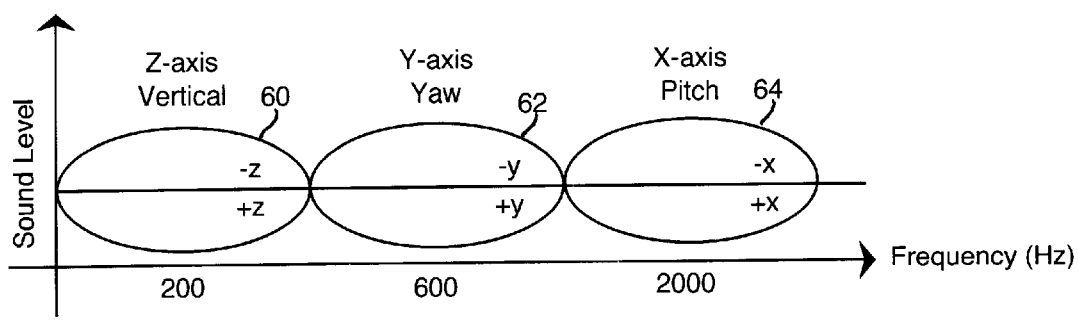
FIG. 5A is a graph illustrating frequency ranges of a white noise signal corresponding to vertical, yaw and pitch motions sensed by the inertia processor according to the present invention.

FIG. 5A is similar to FIG. 4A but illustrates a white noise frequency spectrum in response to motion sensed by the inertia processor 2. In addition, as discussed above, pink, brown or popcorn noise signals may also be used. As shown, the spectral component of the white noise frequency spectrum is divided into three frequency ranges. The white noise frequency spectrum includes a z-axis vertical frequency range 60, a y-axis yaw frequency range 62, and an x-axis pitch frequency range 64. The amplitude of these frequency ranges are altered by the inertia processor 2 in response to the sensed motion. A positive z-axis sensation decreases the amplitude of the z-axis vertical frequency range 60. A negative z-axis sensation increases the amplitude of the z-axis vertical frequency range 60. A yaw to the right decreases the amplitude of the y-axis yaw frequency range 62 and a yaw to the left increases the amplitude of this range. Similarly, a forward pitch results in a decrease. of the amplitude of the x-axis pitch frequency range 64 and a rearward pitch results in an increase in amplitude of this frequency range. In addition, the changes to the amplitudes of the frequency ranges of the white noise are proportional to sensed motion, that is, the greater the sensation, the greater the spectral amplitude change. Again, the proportional relationship is not necessarily linear.

Figure 5B:
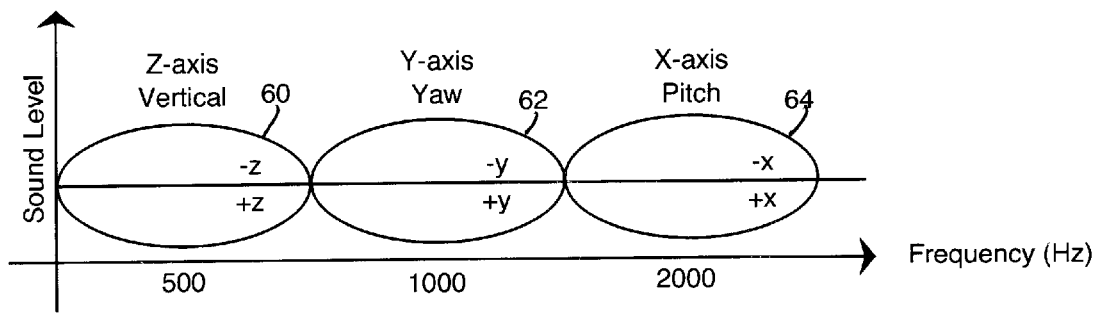
FIG. 5B is another graph illustrating frequency ranges of a white noise signal corresponding to vertical, yaw and pitch motions sensed by the inertia processor according to the present invention.

FIG. 5A illustrates the z-axis vertical frequency range 60, y-axis yaw frequency range 62, and x-axis pitch frequency range 64 centered at 200 Hz, 600 Hz, and 2 KHz, respectively. However, these ranges may be centered at other frequencies. For example, FIG. 5B illustrates the z-axis vertical frequency range 60, the y-axis yaw frequency range 62, and the x-axis pitch frequency range 64 centered at frequencies of 500 Hz, 1000 Hz, and 2000 Hz, respectively. The amplitude of these frequency ranges are altered by the inertia processor 2 in response to a sensed motion, as described in reference to FIG. 5A. Further, the y-axis yaw frequency range 62 is centered at 1000 Hz for similar reasons as that discussed in reference to FIG. 4B. That is, the yaw motion is particularly critical in causing motion sickness and the human ear is particularly sensitive to frequencies around 1000 Hz.

Figure 5C:
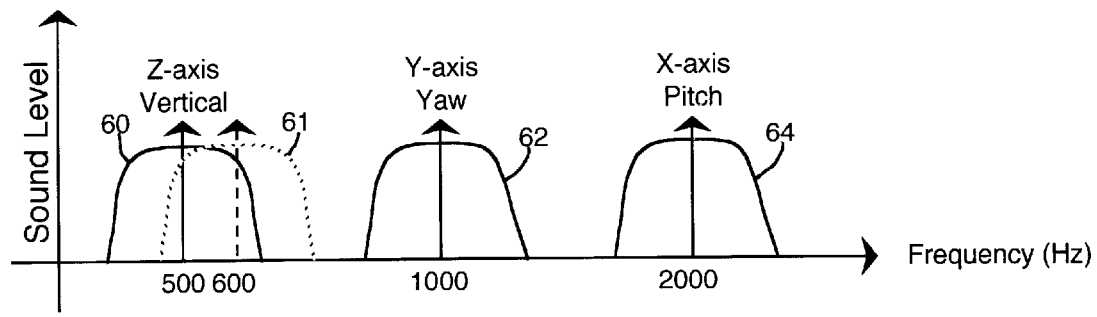
FIG. 5C is yet another graph illustrating frequency ranges of a white noise signal corresponding to vertical, yaw and pitch motions sensed by the inertia processor according to the present invention.

FIG. 5C is yet another graph illustrating frequency ranges of a white noise signal corresponding to vertical, yaw, and pitch motions sensed by the inertia processor shown in FIG. 2B, for example. In particular, FIG. 5C is similar to FIGS. 5A and 5B except that a center frequency of the z-axis vertical frequency range 60, y-axis yaw frequency range 62, and x-axis pitch frequency range 64 shift in response to a sensed motion. That is, the center frequency of the z-axis vertical frequency range 60 (e.g., centered at 500 Hz) increases in frequency when a positive z-axis motion is sensed and decreases in frequency in response to a negative z-axis sensed motion. The z-axis vertical frequency range 61 (illustrated by a dotted line) represents that the z-axis vertical frequency range 60 has been shifted from a center frequency of 500 Hz to a center frequency of 600 Hz. This shift indicates the inertia processor 2 sensed a positive z-axis motion. That is, a positive z-axis motion was sensed by the accelerometer 51. The center frequency of the y-axis yaw frequency range 62 (e.g., centered at 1000 Hz) increases in frequency when the inertia processor 2 is tilted clockwise (when viewed from the front of the device) about the y-axis (i.e., yaw to the right). In addition, the center frequency of the y-axis yaw frequency range 62 decreases in frequency when the inertia processor 2 is tilted counter-clockwise about the y-axis (i.e., yaw to the left). The y-axis yaw frequency range 62 shown in FIG. 5C is centered at 1000 Hz, which represents a yaw to the right, was not sensed by the inclinometer 53 (i.e., the frequency range did not shift). The center frequency of the x-axis pitch frequency tone 64 (e.g., centered at 2 KHz) increases in frequency when the instrument is tilted forward, referred to as a forward pitch, and decreases in frequency when the instrument is tilted backwards, referred to as a rearward pitch. Thus, as shown, the x-axis pitch frequency range 64 has not changed, which indicates the second inclinometer 55 did not detect a pitching motion. In addition, the changes to the frequencies ranges are proportional to the sensed motion, that is, the greater the sensed motion, the greater the change of the frequency range. The sound level (i.e., amplitude) of each frequency range may also be adjusted as described in reference to FIGS. 5A and 5B.

Figure 5D:
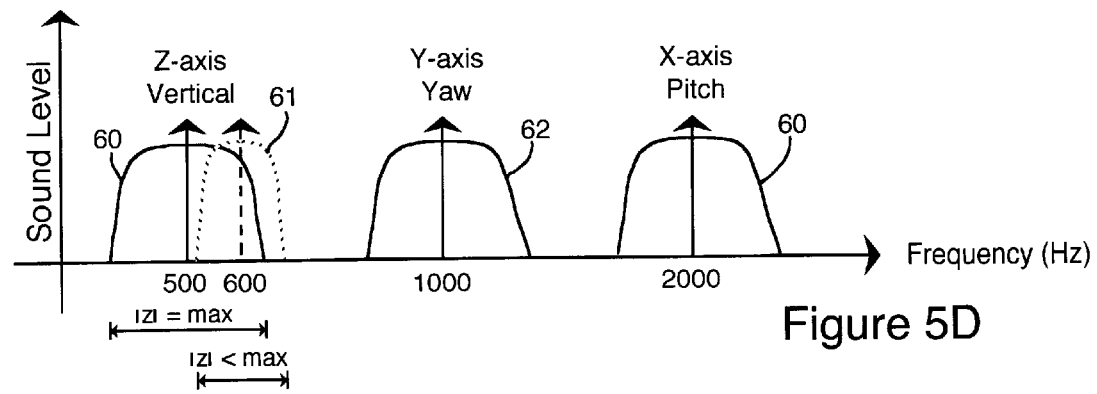
FIG. 5D is still another graph illustrating frequency ranges of a white noise signal corresponding to vertical, yaw and pitch motions sensed by the inertia processor according to the present invention.

FIG. 5D is still another graph illustrating a variation of frequency ranges of a white noise signal corresponding to vertical, yaw and pitch motions sensed by the inertia processor 2. FIG. 5D is similar to FIG. 5C, but a bandwidth of the z-axis vertical frequency range 60, y-axis yaw frequency range 62, and x-axis pitch frequency range 64 also shift in response to a sensed motion. That is, based on a detection motion, the bandwidth may increase or decrease. Thus, for the case of FIG. 5D, the variation in spectral emphasis includes a variation in a bandwidth, a center frequency, and an amplitude of a first range of the sensory signals. For example, as illustrated in FIG. 5D, when the inertia processor 2 senses z-axis vertical data indicating a steady state (i.e., normally level) motion, the bandwidth of the z-axis vertical frequency range 60 is a maximum ($|z|$=max). When the inertia processor 2 senses an increase in the z-axis vertical motion, the bandwidth of the z-axis vertical frequency range 60 decreases ($|z|$<max). The decrease in the bandwidth of the z-axis vertical frequency range is illustrated as a z-axis vertical frequency range 61. Therefore, FIG. 5D illustrates an example of adjusting a bandwidth, a center frequency, and a sound level of the z-axis vertical frequency range 60. Likewise, the y-axis yaw vertical range 62 and the x-axis pitch vertical range 64 may be adjusted.

Further, the bandwidth of the frequency ranges may be selected different than that shown in FIGS. 5A, 5B, 5C, and 5D. In addition, FIGS. 5A, 5B, 5C, and 5D correspond to a property sensed in three degrees of freedom. However, as discussed above, the inertia processor 2 may detect a property in at least six degrees of freedom, and accordingly it is possible to represent these six degrees of freedom by using six frequency ranges of the white noise signal. Further, pink, brown and popcorn noise signals may be used rather than white noise signals.

Figure 6A:
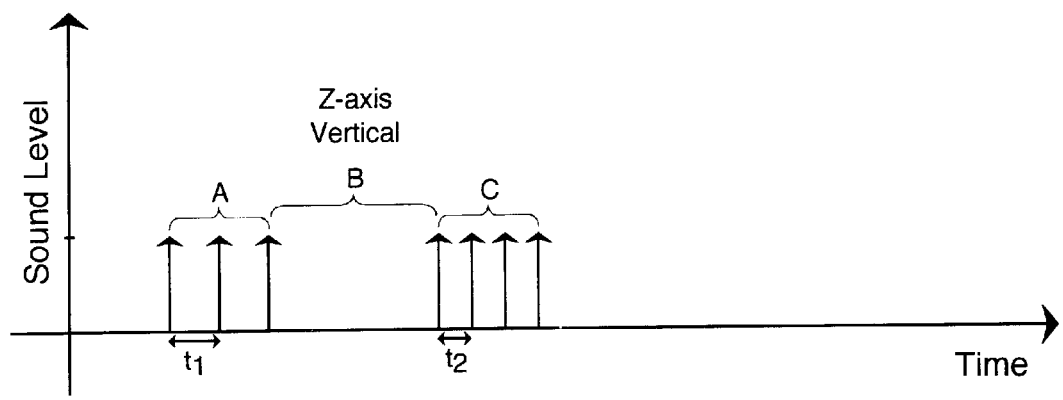
FIG. 6A is a graph illustrating audio tone signals corresponding to a vertical motion sensed by the inertia processor according to the present invention.
Figure 6B:
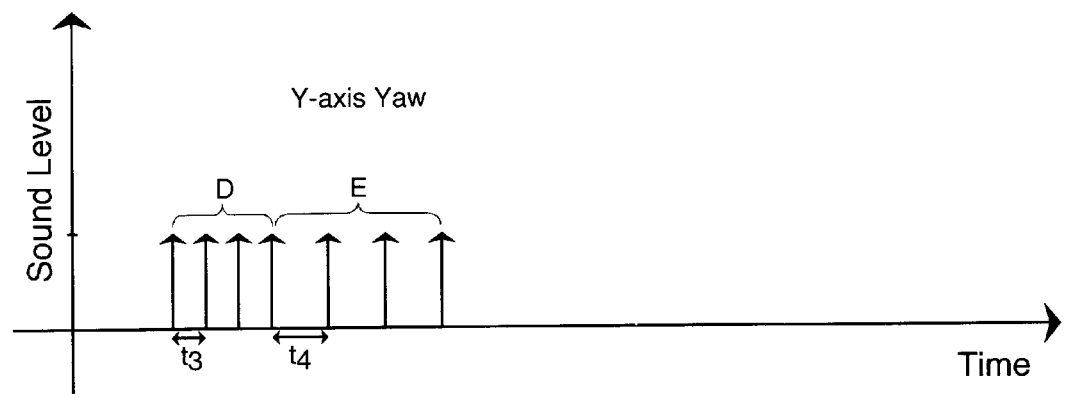
FIG. 6B is another graph illustrating audio tone signals corresponding to a yaw motion sensed by the inertia processor according to the present invention.
Figure 6C:
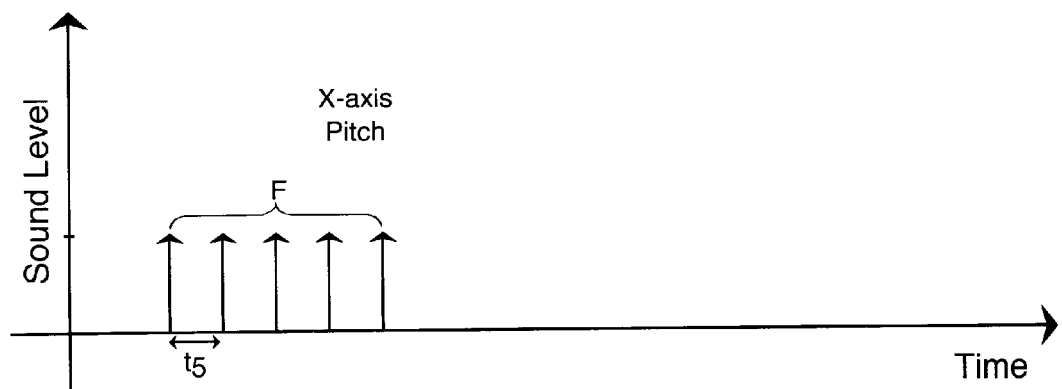
FIG. 6C is yet another graph illustrating sensory signals corresponding to a pitch motion sensed by the inertia processor according to the present invention.

FIGS. 6A–6C illustrate audio tone signals in response to respectively sensed vertical, yaw and pitch motions of an object. For example, as shown in FIG. 6A, the audio tones shown in portion A have a time interval $t_1$. Further, the portion B does not contain audio tones and thus the user would not hear any audio tones. The portion C includes audio tones which are separated by a time interval $t_2$. The audio tone signals shown in portion A may be 500 Hz and the audio tone signal shown in portion C may be 550 Hz, for example. The audio tone signals in portion A correspond to a negative detected z-axis vertical motion and the tone signals shown in portion C correspond to a positive detected z-axis vertical motion. Thus, as shown in FIG. 6A, the user hears the tone signals in portion A separated by time intervals $t_1$ which is due to a negative z-axis vertical detected motion. Then as the object achieves a substantially stable position, the user will hear silence which is illustrated as portion B in the figure. That is, the tone signals only occur when a motion of the object is sensed by the inertia processor 2. Thus, if the object is not moving, the user will not be inundated with tone signals. Further, the tone signals in portion C, which correspond to a positive detected z-axis vertical sense motion, have a smaller time interval $t_2$ than the tone signals in portion A (time intervals $t_1$). The tone signals in portion C have a shorter time interval based on a larger degree of the detected z-axis vertical motion. For example, if a large z-axis vertical motion is detected, the time interval $t_2$ is made shorter so that the user will hear more tone signals than if a smaller z-axis vertical motion is detected. Alternatively, the time intervals may be set to be opposite of that discussed above. That is, the tone signals may be set so that the interval therebetween is larger based on a larger sensed motion.

FIGS. 6B and 6C are similar to FIG. 6A but correspond to y-axis yaw sensed motion and x-axis pitch sensed motion. The tone signals shown in portion D of FIG. 6B may be 1,000 Hz and are separated by a time interval $t_3$. The tone signals shown in portion E may be 1,100 Hz are separated by a time interval $t_4$ The audio tone signals shown in portion F of FIG. 6C may be 2,000 Hz and are separated by a time interval $t_5$. Obviously, alternative frequencies and time intervals can be used for the audio tones. Thus, as shown in FIGS. 6A–6C, as the motion of the object is detected, a plurality of audio tones are intermittently supplied to the user based on the sensed motion of the object.

In addition, it is to be understood that the audio tones may also be audio messages, such as words. For example, the audio tones may be words, such as "left, left, left . . . right, right, right" that are presented to the user based on the sensed motion of the object. The interval between the words may also vary as that described for the audio tones.

The converted sensory signals to be applied via the mechanical and electrical stimulations also have a variation in spectral emphasis in proportion to the sensed motion. The variation in spectral emphasis in this regard includes applying more or less mechanical/electrical stimulation, etc. For example, FIG. 7A illustrates a wrist band 110 having a plurality of mechanical/electrical stimulators 112. For the case of mechanical stimulation, the stimulators 112 may be configured to vibrate or apply pressure to the skin of a user. For the case of electrical stimulation, the stimulators 112 may be configured to provide electrical pulses to the user. Thus, based on a Z-axis vertical motion sensed, the stimulators 112 in that region may be configured to vibrate or apply electrical impulses to the user. Similarly, based on the X-axis pitch and Y-axis yaw motion sensed, the stimulators 112 corresponding to those regions may also be configured to apply an appropriate amount of mechanical or electrical simulation. FIG. 7A illustrates a wrist band, however, a head band or anklet bracelet, etc. may also be used. In addition, the electrical/mechanical stimulators may be adjusted to be faint, noticeable, very strong, etc., by a dial (not shown) on the wristband. The stimulators 112 may be activated via wireless communication with the inertia process using a wireless communication port 114.

FIG. 7B illustrates a pendant receiver/transmitter 120 for presenting sensory signals to the user. As shown, the pendant receiver/transmitter 120 includes a receiver 44, a wireless communication port 124 and headphones 122. The receiver 44 receives sensory signals from the inertia processor 2 and presents the sensory signals to the user via the headphones 122. The wireless communication port 124 is configured to receive the sensory signals from the inertia processor 2 and to transmit these signals to the headphones 122. FIG. 7C illustrates speaker earrings 126 (i.e., earphones) which may be used instead of the headphones 122. Thus, a user may function without the inconvenience of wires or inner ear headphones. The speaker earrings 126 may come in a variety of fashionable looks.

Figure 8:
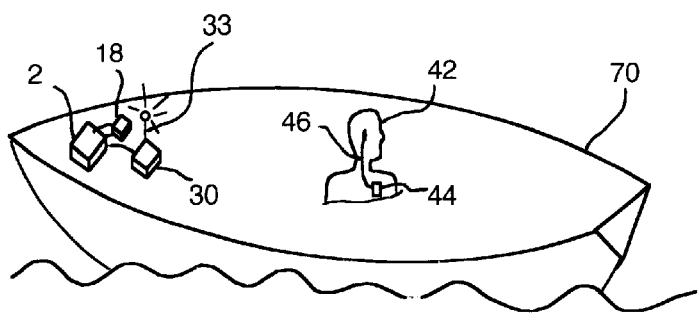
FIG. 8 is a perspective view of the motion sickness apparatus used aboard a ship.

To operate the device of the present invention, the inertia processor 2 may be mounted or placed on a level (normally level) surface of an object and connected to the transmitter 30. One example of using the device of the present invention is shown in FIG. 8. As shown, the inertia processor 2, battery 18, and transmitter 30 are mounted securely in a bow of a boat 70. When the boat 70 moves, the inertia processor 2 senses this motion and converts the sensed motion into corresponding sensory signals. The sensory signals 33 are then transmitted to the receiver 44 which is attached to the user 42. The user 42 hears the sensory signals 33 using, for example, an earphone 46. Thus, the user will, without conscious volition, utilize this accurate new data stream to resolve the conflict between the various ocular, vestibular and proprioceptive inputs via the principle of indeterminacy. The sensory signals 33 may be optical, display, white noise, pink noise, brown noise, popcorn noise, audio tones, mechanical, electrical, etc. or any combination thereof as discussed above. In addition, the sensing mechanism (e.g., inclinometers, accelerometers) may also be disposed at positions on the boat so as to exaggerate a sensed motion.

Figure 9:
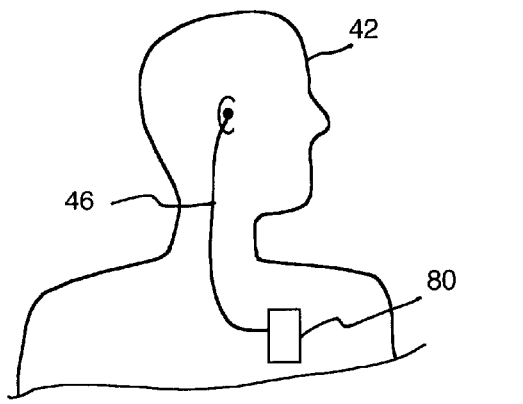
FIG. 9 is a perspective view of the motion sickness apparatus attached to an individual.

FIG. 9 illustrates another use of the device according to the present invention. In this example, the inertia processor 2, battery 18, transmitter 30, and receiver 44 are contained in a single common housing 80. The inertia processor 2 is similar to that shown in FIG. 2A, but includes only the first inclinometer 53 and second inclinometer 55, which detect yaw and pitch motions, respectively (i.e., the accelerometer 51 is not included). Thus, the inertia processor 2 contained in the common housing 80 senses changes in the individual's motion (i.e., y-axis yaw and x-axis pitch motions), converts this sensed motion to corresponding sensory signals, and presents the sensory signals to the user. Further, the device may be placed at various points on the body to accurately reflect positional changes, such as a plurality of sensors placed along the individual's spine. The sensed signals may also be exaggerated as discussed above.

Figure 10:
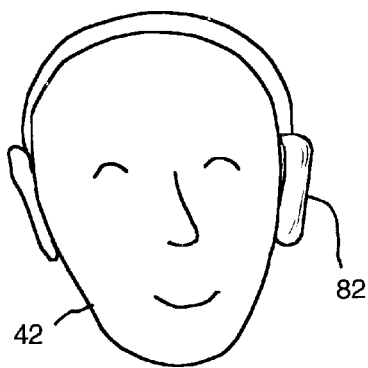
FIG. 10 is a perspective view of the motion sickness apparatus included in a headphone.

FIG. 10 illustrates yet another example in which the device of the present invention may be used. In this example, the inertia processor 2, battery 18, transmitter 30, and receiver 44 are included in a headset 82 so that the movement of the head is sensed rather than the movement of the body. The inertia processor 2 is similar to that discussed for FIG. 9 and senses motion in 2 axes (i.e., yaw and pitch). This illustration is particular useful for individuals which have severe balancing problems. In fact, some individuals with a severe vestibular imbalance become nauseated at the slightest movement of their head. This device can assist that individual in reconciling the conflicts between received vestibular and ocular data.

Figure 11:
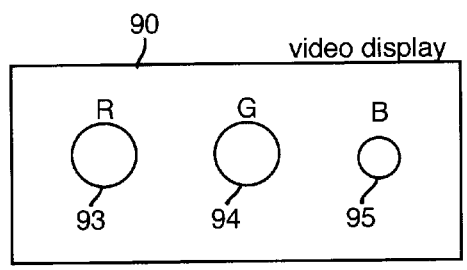
FIG. 11 is a perspective view of the motion sickness device used to project a display signal including display elements on a display.
Figure 11:
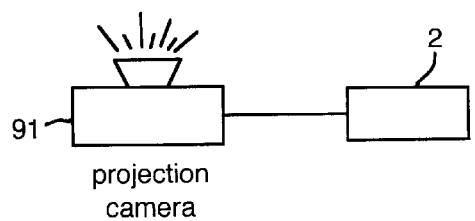

FIG. 11 illustrates another example in which the device may be used. In this example, the inertia processor 2 senses the motion of an object and converts this sensed motion into first, second and third display signals to be displayed as corresponding first, second and third displayed elements on a video display 90. The converted display signals corresponding to the sensed motion is output to, for example, a projection camera 91 via the audio jack of the inertia processor 2. The projection camera 91 projects the display signals as corresponding displayed elements to the video display 90, which a single user or multiple users may be viewing while being aboard, for example, a ship.

The displayed elements may be a variety of colors, each color corresponding to a particular sensed motion. For example, the red, green, and blue colors in a conventional color scheme may correspond to a sensed vertical, yawing, and pitching motion of the object, with the selected colors varying in a display characteristic in proportion to the sensed motion. For example, the red (R) displayed element 93, green (G) displayed element 94, and blue (B) displayed element 95 shown in FIG. 11 may vary, for example, in at least one of intensity, pattern, size, and shade of color based on the respective sensed vertical, yawing, and pitching motion of the object. The displayed elements 93, 94 and 95 are illustrated in FIG. 9 as circles.

However, the displayed elements 93, 94 and 95 may be any symbol, such as a star-shaped symbol, a square-shaped symbol, etc. As shown, the blue (B) displayed element 95 has decreased in size based on a sensed vertical motion (for example, due to a negative pitching motion of the ship). Another example of presenting display signals, which have been converted from sensed motions by the inertia processor, may be achieved by displaying a column of display elements on a left portion of a video display and a row of display elements on a bottom portion of the video display. The column of displayed elements may appear to the viewer as moving vertically in either direction, and the row of displayed elements may appear as moving horizontally in either direction. The column of displayed elements may correspond to the sensed vertical motion and the row of displayed elements may correspond to the sensed yawing motion. The speed and direction that the displayed elements move is based on the sensed motion of the ship. In addition, for the sensed pitching motion, a displayed element which includes a circle with a dot in the center may be displayed in a middle portion of the video display. In this case, the circle may become larger or smaller based on a sensed pitching motion of the stem of the boat, whereas the dot in the center may move up or down, for example, based on a sensed pitching motion of the bow of the boat.

Thus, the individual user or multiple users viewing the display, can use the displayed elements to reconcile a conflict between the vestibular, ocular, and proprioceptive inputs, thus reducing the likelihood of motion sickness. Similarly, a displayed element representing an actual ship, for example, as in a view directly forward from the bow will also accomplish this same conflict resolution.

Figure 12:
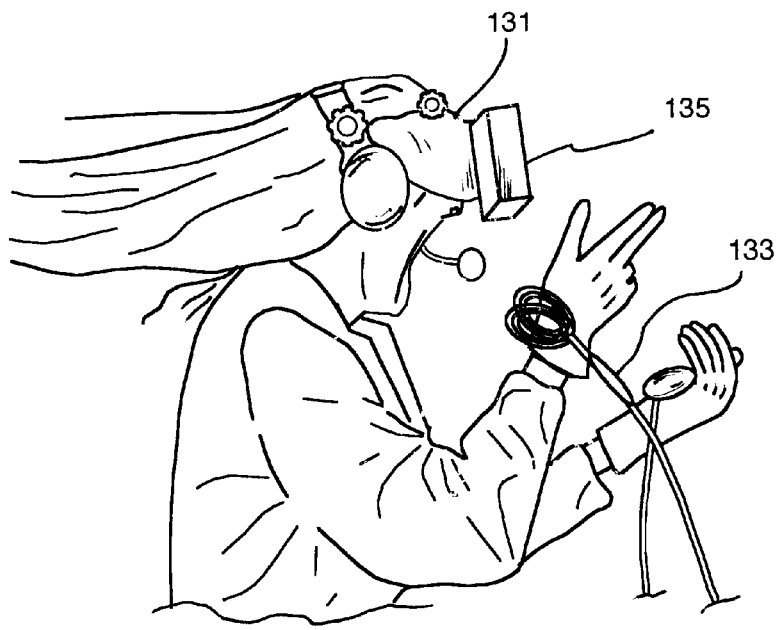
FIG. 12 is a perspective view of the motion sickness apparatus included in a virtual reality device.

FIG. 12 illustrates still another example in which the prevention invention may be used. In this example, the user is operating a virtual reality device 131. The user has control over certain functions (e.g., which direction they "travel" through virtual reality) via a virtual reality control 133. Using the control 133, the user may view different scenes, for example, being displayed in the display 135. Some people feel motion sickness when operating virtual reality devices, or even standard video games.

In virtual reality, the scene being viewed may change based on the movement of the control 133 or the movement of the head. Thus, the sensing converter 2 may sense the motion of the user's head (as discussed with reference to FIG. 10), convert this sensed property to corresponding sensory signals and present the sensory signals to the user. In addition, the movement of the control 133 is already determined by processes of the virtual reality device (i.e., with software algorithms). Thus, this information may be converted to sensory signals and presented to the user.

Figure 13:
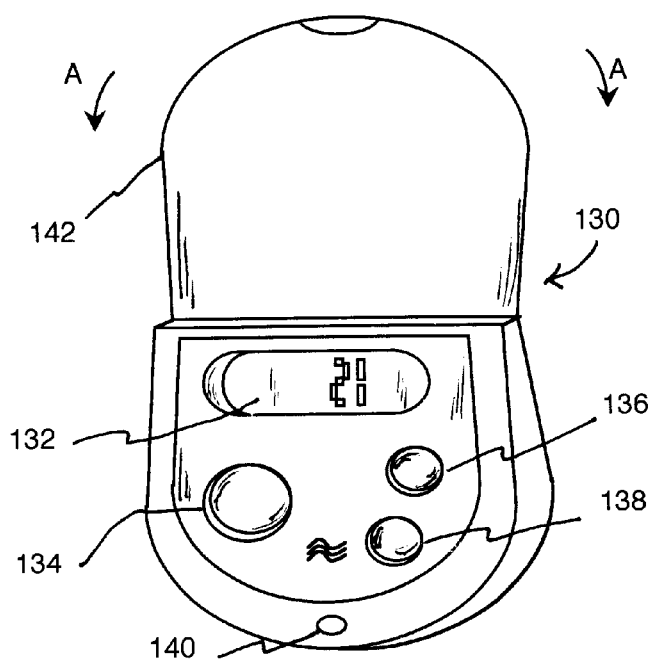
FIG. 13 is a perspective view of a pocket wireless receiver/transmitter according to the present invention.

FIG. 13 illustrates a pocket receiver/transmitter 130, which includes a channel display 132, and ON/OFF button 134, a channel adjust button 136, and a noise adjust mechanism 138. The pocket receiver/transmitter 130 receives sensory signals from the inertia processor 2 via a wireless communication port 140. Further, the pocket receiver/transmitter 130 may transmit the received signals to earphones 126, for example, via the wireless communication port 140. The channel adjust mechanism 136 may be used to change the channel shown in the channel display 21. That is, a user may find better reception on a particular channel, and change the channel using the channel adjust mechanism 136. The noise adjust mechanism 138 may be used to adjust the volume of the audio tones, white noise, and other presenting mechanisms. The ON/OFF button 130 may be used to turn ON or OFF the pocket receiver/transmitter 130. Further, the pocket receiver transmitter 130 may be included in a leather case 142, which may be foldable (as shown by arrows A) so as to cover the channel display 132, ON/OFF button 130, etc.

A method of relieving motion sickness will now be described with reference to FIGS. 1, 3 and 4. The inertia processor 2 is used for sensing a property of an object and for converting the sensed property to corresponding sensory signals. As discussed above, the audio, white noise, pink noise, brown noise and popcorn noise sensory signals mechanical/electrical stimulations have a variation in spectral emphasis in proportion to the sensed property. In addition, the display signals have a variation in a display characteristic and the audio tone signals may have a variation in time intervals between successive audio tones based on the sensed property of the object.

Further, the method of converting includes presenting the sensory signals using, for example, the transmitter 33 and the receiver 44. In one example, the method of converting includes varying a frequency of a first signal within a first predetermined range around a first center frequency in proportion to a sensed pitching motion of the object, and varying a frequency of a second signal within a second predetermined range around a second center frequency in proportion to a sensed yawing motion of the object. In another example, the method of converting includes varying a spectral emphasis of a first frequency range of white, pink, brown or popcorn noise signals in proportion to a sensed pitching motion of the object, and varying a spectral emphasis of second frequency range of the white, pink, brown or popcorn noise signals in proportion to a sensed yawing motion of the object.

The variation in spectral emphasis includes, but is not limited to, a variation in a bandwidth, a center frequency, and an amplitude of a first range of the sensory signals. In addition, the method of converting also includes generating display elements which correspond to the sensed sensory signals. For the case of display signals, the display signals vary in a display characteristic in proportion to the sensed motion of the object. The method of converting also includes generating audio tone signals which correspond to the sensed sensory signals. For the case of the audio tone signals, the audio tone signals have a variation in time intervals between successive audio tones based on the sensed motion of the object.

Further, the present inventor has determined that low frequency horizontal movements appear to be most related to motion sickness. By providing a device which includes a sensor to detect these movements, and a sensory converter coupled to the sensor, as discussed above, the present invention reduces the effect of motion sickness.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent in the United States is:

1. An apparatus for relieving motion sickness, comprising:
   at least one sensor which senses a property of an object;
   a sensory converter coupled to said sensor and configured to convert said sensed property to corresponding sensory signals having a variation in spectral emphasis in proportion to said sensed property; and
   a presentation mechanism configured to present said sensory signals to a user.

2. The apparatus according to claim 1, wherein the at least one sensor includes at least one of 1) an accelerometer, 2) a gyro, 3) a GPS control unit, 4) a strain gauge, 5) an inclinometer, 6) an atmospheric control unit, 7) a pressure control unit and 8) a simulating control unit.

3. The apparatus according to claim 1, wherein the at least one sensor includes three accelerometers configured to respectively sense a pitch, yaw and roll of the object.

4. The apparatus according to claim 1, wherein the presentation mechanism includes a wireless communication port configured to present the sensory signals to the user.

5. The apparatus according to claim 1, wherein the presentation mechanism includes at least one of 1) an earphone, 2) a headphone, 3) a display, 4) a speaker, 5) a mechanical/electrical wristband or headband and 6) speaker earrings.

6. The apparatus according to claim 1, further comprising:
   a pendant receiver/transmitter configured to receive the sensory signals from the sensory converter and to transmit the received sensory signals to the user via the presentation mechanism.

7. The apparatus according to claim 1, further comprising:
   a pocket receiver/transmitter configured to receive the sensory signals from the sensory converter and to transmit the sensory signals to the user via the presentation mechanism.

8. The apparatus according to claim 7, wherein the pocket receiver comprises:
   a channel selector configured to select a channel on which to receive the sensory signals from the sensory converter;
   an ON/OFF mechanism configured to turn ON and OFF the pocket receiver/transmitter;
   a volume mechanism configured to adjust a volume of the pocket receiver/transmitter;
   a display configured to display the channel selected by the channel selector; and
   a wireless communication port configured to receive/transmit the sensory signals.

9. The apparatus according to claim 1, further comprising:
   an exaggeration mechanism configured to exaggerate the properties of the object sensed by the at least one sensor.

10. The apparatus according to claim 9, wherein the exaggeration mechanism includes a computer process configured to exaggerate the properties of the object sensed by the at least one sensor.

11. The apparatus according to claim 1, wherein the at least one sensor is disposed at positions on said object such that the sensed properties of the object are exaggerated.

12. The apparatus according to claim 1, further comprising:

at least one ON/OFF switch respectively corresponding to said at least one sensor, said sensory converter and said presentation mechanism, and configured to turn ON and OFF the respective said at least one sensor, said sensory converter and said presentation mechanism.

13. The apparatus according to claim 1, wherein the apparatus is disposed on at least one of 1) an airplane, 2) a ship, 3) an elevator, and 4) a submarine.

14. The apparatus according to claim 1, wherein the apparatus is included with a virtual reality game or video game.

15. The apparatus according to claim 1, wherein the sensory converter comprises:
a first mechanism configured to vary said spectral emphasis including at least one of 1) a bandwidth and 2) a center frequency of a first frequency range of said sensory signals in proportion to a sensed pitching motion of said object; and
a second mechanism configured to vary said spectral emphasis including at least one of 1) a bandwidth and 2) a center frequency of a second frequency range of said sensory signals in proportion to a sensed yawing motion of said object.

16. The apparatus according to claim 1, wherein said at least one sensor senses said motion in at least one of six degrees of freedom.

17. The apparatus according to claim 1, wherein said at least one sensor, said sensory converter, and said presentation mechanism are included in a common housing.

18. A method for relieving motion sickness, comprising:
sensing a property of an object;
converting said motion sensed in said sensing step to corresponding sensory signals having a variation in spectral emphasis in proportion to said sensed property; and
presenting said sensory signals to a user.

19. The method according to claim 18, wherein the sensing step senses the property of the object via at least one of 1) an accelerometer, 2) a gyro, 3) a GPS control unit, 4) a strain gauge, 5) an inclinometer, 6) an atmospheric control unit, 7) a pressure control unit and 8) a simulating control unit.

20. The method according to claim 18, wherein the sensing step senses the property of the object via three accelerometers configured to respectively sense a pitch, yaw and roll of the object.

21. The method according to claim 18, wherein the presenting step presents the sensory signals to the user via wireless communication.

22. The method according to claim 18, wherein the presenting step presents the sensory signals to the user via at least one of 1) an earphone, 2) a headphone, 3) a display, 4) a speaker, 5) a mechanical/electrical wristband or headband and 6) speaker earrings.

23. The method according to claim 18, further comprising:
receiving the sensory signals from the sensory converter via a pendant receiver/transmitter.

24. The method according to claim 18, further comprising:
receiving the sensory signals from the sensory converter a pocket receiver/transmitter.

25. The method according to claim 24, wherein the pocket receiver/transmitter comprises:
a channel selector configured to select a channel on which to receive the sensory signals from the sensory converter;
an ON/OFF mechanism configured to turn ON and OFF the pocket receiver/transmitter;
a volume mechanism configured to adjust a volume of the pocket receiver/transmitter;
a display configured to display the channel selected by the channel selector; and
a wireless communication port configured to receive/transmit the sensory signals.

26. The method according to claim 18, further comprising:
exaggerating the properties of the object sensed in the sensing step.

27. The method according to claim 26, wherein the exaggerating step includes a computer process configured to exaggerate the properties of the object sensed by the sensing step.

28. The method according to claim 18, wherein the sensing step senses the property of the object via at least one sensor disposed at positions on said object such that the sensed properties of the object are exaggerated.

29. A system for relieving motion sickness, comprising:
means for sensing a property of an object;
means for converting said motion sensed in said sensing means to corresponding sensory signals having a variation in spectral emphasis in proportion to said sensed property; and
means for presenting said sensory signals to a user.

30. The system according to claim 29, wherein the sensing means senses the property of the object via at least one of 1) an accelerometer, 2) a gyro, 3) a GPS control unit, 4) a strain gauge, 5) an inclinometer, 6) an atmospheric control unit, 7) a pressure control unit and 8) a simulating control unit.

31. The system according to claim 29, wherein the sensing means senses the property of the object via three accelerometers configured to respectively sense a pitch, yaw and roll of the object.

32. The system according to claim 29, wherein the presenting means presents the sensory signals to the user via wireless communication.

33. The system according to claim 29, wherein the presenting means presents the sensory signals to the user via at least one of 1) an earphone, 2) a headphone, 3) a display, 4) a speaker, 5) a mechanical/electrical wristband or headband and 6) speaker earrings.

34. The system according to claim 29, further comprising:
means for receiving the sensory signals from the sensory converter via a pendant receiver/transmitter.

35. The system according to claim 29, further comprising:
means for receiving the sensory signals from the sensory converter a pocket receiver/transmitter.

36. The system according to claim 35, wherein the pocket receiver/transmitter comprises:
means for selecting a channel on which to receive the sensory signals from the sensory converter;
means for turning ON and OFF the pocket receiver/transmitter;
means for adjusting a volume of the pocket receiver/transmitter;
means for displaying the channel selected by the channel selector; and
wireless communication means for receiving/transmitting the sensory signals.

37. The system according to claim 29, further comprising:
means for exaggerating the properties of the object sensed in the sensing step.

38. The system according to claim 37, wherein the exaggerating means includes computer process means for exaggerating the properties of the object sensed by the sensing means.

39. The system according to claim 29, wherein the sensing means senses the property of the object via at least one sensor disposed at positions on said object such that the sensed properties of the object are exaggerated.

* * * * *